US008871450B2

(12) United States Patent
Hacker et al.

(10) Patent No.: US 8,871,450 B2
(45) Date of Patent: Oct. 28, 2014

(54) BIOMARKER FOR COLORECTAL CANCER

(75) Inventors: Ulrich Hacker, Cologne (DE); Valentin Goede, Cologne (DE); Oliver Coutelle, Cologne (DE)

(73) Assignee: Universität zu Köln, Cologne (DE)

( * ) Notice: Subject to any disclaimer, the term of this patent is extended or adjusted under 35 U.S.C. 154(b) by 62 days.

(21) Appl. No.: 13/390,532

(22) PCT Filed: Sep. 6, 2010

(86) PCT No.: PCT/EP2010/063013
§ 371 (c)(1),
(2), (4) Date: Feb. 15, 2012

(87) PCT Pub. No.: WO2011/026962
PCT Pub. Date: Mar. 10, 2011

(65) Prior Publication Data
US 2012/0142012 A1 Jun. 7, 2012

(30) Foreign Application Priority Data

Sep. 7, 2009 (EP) .................................... 09011423

(51) Int. Cl.
*G01N 33/53* (2006.01)
*G01N 33/574* (2006.01)

(52) U.S. Cl.
CPC ...... *G01N 33/57419* (2013.01); *G01N 2800/52* (2013.01); *G01N 2800/56* (2013.01); *G01N 2333/515* (2013.01)
USPC ........................................................ 435/7.1

(58) Field of Classification Search
CPC ................................................... A61K 39/00
See application file for complete search history.

(56) References Cited

FOREIGN PATENT DOCUMENTS

| WO | 00/64946 | 11/2000 |
| WO | 2006/069073 | 6/2006 |

OTHER PUBLICATIONS

Anargyrou et al (Haematologica, 2008, 93(3): 451-454).*
Caine et al (Cancer Letters, 2007, 296-301).*
Park et al (Chest, 2007, 132(1): 200-206).*
Jo et al (Ann Surg Oncol, 2009, 16(7): 2052-2057).*
Kumara et al (Ann Surg, 2009, 249(6): Abstract).*
Caine et al (Eur J Clin Invest, 2003, 33(10): 883-890).*
Fürstenberger et al (Br J Cancer, 2006, 94(4): 524-531).*
Ochiumi et al; "Clinical Significance of Angiopoietin-2 Expression at the Deepest Invasive Tumor Site of Advanced Colorectal Carcinoma"; International Journal of Oncology, vol. 24, No. 3, Mar. 2004, pp. 539-547.
Holash et al.; "Vessel Cooption, Regression, and Growth in Tumors Mediated by Angiopoietins and VEGF"; Science, American Association for the Advancement of Science, vol. 284, No. 5422, Jun. 18, 1999, pp. 1994-1998.
Kumara et al.; "Colorectal Resection is Associated with Persistant Proangiogenic Plasma Protein Changes: Postoperative Plasma Stimulates In Vitro Endothelial Cell Growth, Migration, and Invasion"; Annals of Surgery, vol. 249, No. 6, Jun. 2009, pp. 973-977.
Fayette et al.; "Use of Angiogenesis Inhibitors in TumourTreatment"; European Journal of Cancer, vol. 41, No. 8, May 1, 2005, pp. 1109-1116.
Tait et al; "Angiopoietins in Tumours: The Angiogenic Switch"; Journal of Pathology, vol. 204, No. 1, Sep. 2004, pp. 1-10.
Holash et al.; "New Model of Tumor Angiogenesis: Dynamic Balance Between Vessel Regression and Growth Mediated by Angiopoietins and VEGF"; Oncogene, vol. 18, No. 38, Sep. 20, 1999, pp. 5356-5362.
Gu et al.; "Hypoxia-Induced Up-Regulation of Angiopoietin-2 in Colorectal Cancer"; Oncology Reports, vol. 15, No. 4, Apr. 2006, pp. 779-783.
Helfrich et al.; "Angiopoietin-2 Levels are Associated with Disease Progression in Metastatic Malignant Melanoma"; Clinical Cancer Research 2009, vol. 15, No. 4, Feb. 15, 2009, pp. 1384-1392.
Park et al.; "Serum Angiopoetin-2 as a Clinical Marker for Lung Cancer"; Chest, vol. 132, Jul. 2007, pp. 200-206.

* cited by examiner

*Primary Examiner* — Sean Aeder
(74) *Attorney, Agent, or Firm* — Whitham Curtis Christofferson & Cook, PC (57) ABSTRACT

The present invention relates to new methods for predicting the clinical outcome or determining the treatment course in a subject afflicted with solid tumors, like colorectal cancer, and for monitoring the progression of solid tumors, like colorectal cancer, in a subject. Moreover, the present invention relates to a method for stratification of therapy regimen of a subject afflicted with solid tumor entities, such as colorectal cancer, for determining its susceptibility to the treatment with an inhibitor of angiogenesis. Further, the present invention relates to kits allowing performance of the above methods. In particular, the present invention is based on the finding that determining the level or amount of angiopoietin-2 protein in a sample of a subject is useful for conducting the above referenced methods.

10 Claims, 5 Drawing Sheets

BIOMARKER FOR COLORECTAL CANCER

The present invention relates to new methods for predicting the clinical outcome or determining the treatment course in a subject afflicted with solid tumors, like colorectal cancer, and for monitoring the progression of solid tumors in a subject. Moreover, the present invention relates to a method for the stratification of therapy regimen of a subject afflicted with solid tumor entities, like colorectal cancer, for determining its susceptibility to the treatment with an inhibitor of angiogenesis. Further, the present invention relates to kits allowing performance of the above methods. In particular, the present invention is based on the finding that determining the level or amount of angiopoietin-2 protein in a sample of a subject is useful for conducting the above referenced methods.

BACKGROUND OF THE INVENTION

Screening and monitoring assays are essential for the diagnosis and management of cancer. Cancer screening and monitoring tests, such as blood tests collected in a medical environment, can be useful for large scale screening of clinical healthy (or "asymptomatic") individuals, for diagnosis, for prediction tests or for disease monitoring in subjects. Blood based remote samples for such applications have the advantage that it is convenient for a subject to provide a sample and the risk of side effects is extremely low. Therefore compliance is improved in a test population.

Clinically, tumors are defined as an abnormal mass. Solid tumors may be malignant tumors, consisting of malignant cells and a tumor stroma, thus being cancer. Different types of solid tumors include sarcomas derived from mesenchymal cells and carcinomas, derived from epithelial cells. The most common types of solid tumors are breast cancer, lung cancer, colorectal cancer and prostate cancer. Other solid tumors are gastric cancer, pancreatic cancer, hepatocellula, head and neck cancer, renal cell cancer, cancers of the female reproductive tract like ovarian cancer or endometrial or cervical cancer and germ cell tumors but also skin cancer including basal cell carcinoma, squamous cell carcinoma and malignant melanoma.

In the case of colorectal cancer (CRC), as a representative of solid tumors, only about 30% of people at risk are screened, partly due to psychological barriers induced by uncomfortable and invasive screening methods, such as colonoscopy.

However, CRC including colon cancer (i.e. large bowel cancer) and rectal cancer is the cause of over 655,000 deaths worldwide per year and represents the third most common form of cancer and the second leading cause of cancer-related death in the Western world. Typically, the diagnosis of colon cancer is made by colonoscopy in combination with a tissue biopsy. In loco regional disease, resection of the tumor and adjacent lymph nodes represents a standard of care. In colon cancer, surgery is followed by adjuvant chemotherapy in stage III disease (positive lymph nodes). In locally advanced rectal cancer, cT2/3, cN+ neoadjuvant radiochemotherapy is administered prior surgery.

As it is the case for various solid tumor entities, CRC can take many years to develop and an early detection of CRC significantly improves the chances of cure. For example, there are several different tests available for screening of CRC including digital rectal examination, the fecal occult blood test and various methods of endoscopy. As indicated before, colonoscopy represents the typical method of diagnosis. Moreover, certain biomarkers have been described which should be useful in the context of CRC, e.g. carcinoembryonic antigen (CEA) in the blood that is mainly used during follow up after curative or palliative treatment of CRC. Moreover, stool testing for occult blood and DNA are employed as screening methods for CRC. However, most of these tests do not allow differentiation between different stages of cancer.

For monitoring CRC, in particular during therapy, CEA may be used to monitor and assess response to treatment in patients with metastatic diseases. CEA can also be used to monitor the recurrence in patients post-operatively.

As in most solid tumors, colon cancer staging aims to determine the extent and distribution of disease (i.e. locoregional infiltration of the bowel wall and involvement of locoregional lymph nodes or presence and localization of distant metastasis).

It is performed during the diagnostic work-up and is a prerequisite to determine the optimal treatment strategy. Furthermore, staging is an important determinant of prognosis. The systems for staging CRC describe the extent of local invasion, the degree of lymph node involvement and whether there are distant metastases. For CRC, the most common staging system is the TNM (for tumors/nodes/metastases) system of the American Joint Committee on Cancer. The TNM system assigns a number based on three categories where "T" denotes the degree of invasion of the intestinal wall, "N" the degree of lymphatic node involvement, and "M" the degree of metastases. The broader stage of a cancer is usually quoted as a number—I, II, III, IV—derived from the TNM value grouped by prognosis; a higher number indicates a more advanced cancer and likely a worse outcome. The staging system is provided in the table below.

| AJCC stage | TNM stage | TNM stage criteria for colorectal cancer |
| --- | --- | --- |
| Stage 0 | T is N0 M0 | T is: Tumor confined to mucosa; cancer-in-situ |
| Stage I | T1 N0 M0 | T1: Tumor invades submucosa |
| Stage I | T2 N0 M0 | T2: Tumor invades muscularis propria |
| Stage II-A | T3 N0 M0 | T3: Tumor invades subserosa or beyond (without other organs involved) |
| Stage II-B | T4 N0 M0 | T4: Tumor invades adjacent organs or perforates the visceral peritoneum |
| Stage III-A | T1-2 N1 M0 | N1: Metastases to 1 to 3 regional lymph nodes. T1 or T2. |
| Stage III-B | T3-4 N1 M0 | N1: Metastases to 1 to 3 regional lymph nodes. T3 or T4. |
| Stage III-C | any T, N2 M0 | N2: Metastases to 4 or more regional lymph nodes. Any T. |
| Stage IV | any T, any N, M1 | M1: Distant metastases present. Any T, any N. |

According to the present invention, the term "advanced colorectal cancer" refers to stage IV of the above table following the TNM staging system.

The appropriate treatment of a particular cancer depends on its TNM stage. If CRC is detected at an early stage, it can be curable. However, if it is detected at later stages (when distant metastases are present) it is less likely to be curable. Surgery remains the primary treatment while chemotherapy and/or radiotherapy may be recommended depending on the individual patient's staging and other medical factors. Recently, the overall survival time of patients with CRC, i.e. stage IV, has increased due to the development of novel therapeutic strategies combining chemotherapy, e.g. 5-fluorouracil, irinotecan, oxaliplatin, with e.g. antibodies against epidermal growth factor receptor (EGFR) or vascular endothelial growth factor (VEGF), i.e., antibodies representing and acting as inhibitors of angiogenesis. However, these novel approaches are associated with increased toxicity and cost. Therefore, it is crucial to define biomarkers that can help identifying those patients who benefit most from such targeted therapies.

In colon cancer, chemotherapy after surgery is usually only given if the cancer has spread to the lymph nodes, i.e. at stages III or if distant metastasis is present, stage IV. Recently, it has been described that CRC patients that have a mutation in the k-ras gene do not respond to certain therapies, e.g. those that inhibit the epidermal growth factor receptor, e.g. cetuximab and panitumumab. Moreover, the b-raf oncogene as well as the k-ras oncogene have been utilised to predict outcome of EGFR antibody treatment in patients with metastatic CRC.

The VEGF antibody bevacizumab targets tumor angiogenesis. Presently, the first line chemotherapy regimens involve the combination of intravenous 5-fluorouracil, leucovorin and oxaliplatin with bevacizumab or alternatively, 5-fluorouracil, leucovorin and irinotecan with bevacizumab. The oral fluoropyrimidine capecitabin has been demonstrated to be equally effective as 5-fluorouracil, leucovorin and, therefore, combination chemotherapy with capecitabin and oxaliplatin or irinotecan is also widely used as a chemotherapy backbone. It has been demonstrated that a combination of chemotherapy plus bevacizumab significantly improves progression-free survival compared with chemotherapy alone and has become standard of care in the first and second line treatment of CRC (e.g. Saltz, L. B. et. al., 2008, J. Clin. Oncol. 26:2013-9). Clinical data indicate that bevacizumab without chemotherapy is not successful in treating solid tumors except for renal cell carcinomas (i.e. in combination with interferon-alpha) and possibly hepatocellular carcinoma.

However, in a recent phase III clinical trial response rates were comparable in both treatment arms (38% with and without bevacizumab, Saltz et. al. supra). Clinically, the identification of patients who are likely to respond to bevacizumab-containing treatment could be valuable particularly in patients who may undergo secondary resection of liver metastasis. While k-ras predicts the response for EGFR antibody treatment, equivalent biomarkers for bevacizumab in CRC patients are currently lacking.

The therapeutic blockade of VEGF by bevacizumab in CRC patients induces complex changes in a tumor stromal compartment including the loss of chaotic microvessels, remodeling of the vascular wall and a reduction in the interstitial fluid pressure. Such stromal alterations are part of the vascular "normalisation" process induced by bevacizumab and contribute to more efficient delivery of chemotherapeutic agents.

Angiopoietin-2 (Ang-2) is an inhibitory ligand of the Tie-2 receptor. The functional blockade of Tie-2 receptor tyrosine kinase by Ang-2 results in "abnormal" vessels due to the disruption of vascular wall integrity. In contrast to Ang-2, angiopoietin-1 (Ang-1) represents an agonistic ligand of Tie-2. Angiopoietins are glycoproteins that are involved in vascular development and angiogenesis. At present, four angiopoietins are known, named angiopoietin-1 to angiopoietin-4. Ang-2 is released in response to stimuli, such as injury, hypoxia and bacterial infection, and primes the endothelial activation response and promotes vascular permeability. Elevated Ang-2 levels have been described in patients with severe compared to mild sepsis. Elevated serum concentration levels of Ang-2 have been reported for patients with cancers other than CRC such as non-small cell line cancer and melanoma, where high serum Ang-2 levels are supposed to correlate with disease stage and poor survival (Park J. H., et. al., 2007, Chest 132:200-6; Helfrich I., et. al., 2009, Clin. Cancer Res. 15:1384-92).

Ochiumi, T., et al, 2004, Int. J. Oncol., 24, 539-547, suggest that Ang-2 expression in collaboration with VEGF expression at the deepest invasive site may be correlated with invasive/malignant potential and prognosis of advanced CRC. Both VEGF and Ang-2 are speculated as being correlated with tumor potential and prognosis. Holasch, J., et al., 1999-284, 1994-1998 describe vessel cooption, regression, and growth in tumors mediated by Angiopoietin and VEGF. It is speculated that Ang-2 may prove to be useful in the imaging of very small tumors and metastases.

In WO2006/069073 A2 the use of angiopoietins in anti-tumor therapy is described. A method for decreasing tumor growth is described wherein the amount of pericytes within vessels of the tumor is increased leading to a more mature status of the vessels, hence, improving the effects of the following radiation therapy.

In case of CRC, survival is directly related to the tumor stage at the time of detection. Survival rates for early tumor stages are about 5-times higher than for late stage cancers. Today, the CEA level is used to evaluate the response to surgical and non-surgical types of therapy. The CEA level is thought to correlate with the bulk of the tumor tissue. However, there are colorectal cancers that do not secret CEA into the blood stream.

Accordingly, there is a need in the art for approaches that afford detection and allow determination of the treatment regimen of solid tumors, in particular, CRC, having the added benefit of being cost effective, rapid, and minimally invasive, preferably non-invasive. Approaches that determine the prognosis of cancer and clinical outcome as well as allowing monitoring of treatment response and detecting relapse of cancers are of additional value and can help identifying those patients who benefit most from specific types of therapy as well as identifying the best therapeutic regimen for the individual patient.

There is also a need for allowing follow-up or monitoring the progression of CRC as well as for stratification of a subject with CRC, e.g. according to the treatment response of said subject using biomarkers, preferably by a non-invasive and cost effective method or system allowing the same.

For example, the combination of chemotherapy with the VEGF antibody bevacizumab has become standard in the first line treatment of metastatic CRC, however biomarkers predicting which patients are likely to benefit from these therapies remain elusive. It has already been demonstrated that tissue and plasma levels of VEGF in particular are not predictive of outcome in CRC patients treated with chemotherapy and bevacizumab.

The present invention aims for providing a new biomarker particularly useful in the issues described above.

SUMMARY OF THE PRESENT INVENTION

In a first aspect, the present invention relates to a method for the stratification of the therapeutic regimen of a subject with solid tumors, in particular, with colorectal cancer (CRC), breast cancer (BC) or gastric cancer (GC) determining whether said subject is susceptible to the treatment with an inhibitor of angiogenesis, in particular an inhibitor of VEGF, comprising
a) determining the level or amount of angiopoietin-2 (Ang-2) in a sample of said subject; and
b) determining the susceptibility of said subject to a therapy based on inhibitors of angiogenesis, in particular an inhibitor of VEGF, based on the level or amount of Ang-2.

In a further aspect, the present invention relates to a method for predicting a clinical outcome or determining the treatment course in a subject with solid tumors, in particular, with CRC, BC or GC like CRC of stages III and IV, preferably, of advanced colorectal cancer (stage IV). Said method comprises the steps of
a) determining the amount of Ang-2 in at least one sample of the body fluid of said subject and
b) predicting the clinical outcome or determining treatment course based on the amount of Ang-2 present in said sample.

A further embodiment of the present invention relates to a method for monitoring the progression of solid tumors, in particular, CRC, BC or GC in a subject. Said method comprises the step of
a) detecting the level or amount of Ang-2 in a first sample from the subject at a first point in time;
b) determining the level or amount of Ang-2 in a second sample from the subject at a second point in time; and
c) comparing the level or amount of Ang-2 determined in step a) to the level or amount detected in step b) or to a reference value.

Another embodiment of the present invention relates to a method of diagnosing or identifying advanced CRC in a subject. Said method comprises the step of
a) determining the level or amount of Ang-2 in a sample of the body fluid of said subject; and
b) comparing the level or amount determined in step a) to a reference value,
wherein an increased level or amount relative to the reference value is indicative of advanced CRC in said subject.

That is, the present inventors recognized that Ang-2 present in the body fluid of a subject with solid tumors, in particular, with CRC, BC or CG, represents a suitable biomarker for predicting the clinical outcome and monitoring response to therapy. In particular, it has been identified that an increased amount of Ang-2 in a body fluid sample of a subject, in particular, in a blood sample, like a serum or plasma sample, allows determination of the treatment course and prediction of the clinical outcome of subjects with solid tumors, such as CRC, BC or GC, in particular with CRC of stage IV as well as the stratification of the therapeutic regimen.

Moreover, the present invention relate to the use of a kit, in particular, a test kit for determining whether a subject has a risk for developing advanced CRC, BC or GC, or for predicting a clinical outcome or determining the treatment course in a subject with solid tumors, such as CRC, or for the stratification of a subject with solid tumors, such as CRC, BC or GC to determine whether said subject is susceptible to the treatment with inhibitors of angiogenesis, in particular with inhibitors of the vascular endothelial growth factor (VEGF), or for monitoring the progression of solid tumors, such as CRC, BC or GC in a subject, comprising means for determining the level or amount of Ang-2 protein in a body fluid sample of a subject to be tested and instructions on how to use said test kit for a method according to the present invention.

DETAILED DESCRIPTION OF THE PRESENT INVENTION

The present invention relates in a first aspect to a method for the stratification of a subject with solid tumors, such as CRC, BC or GC, for determining whether said subject is susceptible to the treatment with an inhibitor of angiogenesis, in particular an inhibitor of the vascular endothelial growth factor (VEGF), comprising the steps of
a) determining the level or amount of Ang-2 in a sample of said subject; and
b) determining the susceptibility of said subject to a therapy based on inhibitors of angiogenesis, in particular an inhibitor of VEGF, based on the level or amount of Ang-2.

That is, the present inventors recognized that depending on the level or amount of Ang-2 in a body fluid sample of a subject with solid tumors, such as CRC, BC or GC the therapeutic regimen may be customized or personalized accordingly. Namely, the present inventors identified that in contrast to the common view, at increased level of Ang-2 in the serum of subjects with solid tumors, such as CRC, BC or GC said subjects are not susceptible to the treatment with an inhibitor of angiogenesis, in particular, an inhibitor of VEGF, like bevacizumab. Although, said subjects may be treated successfully with a combination of an inhibitor of angiogenesis, like an inhibitor of VEGF, e.g. bevacizumab, and inhibitors of Ang-2, like Ang-2 antibodies, e.g. as described in WO2007089445.

As used herein, the term "susceptible to the treatment" refers to the situation where in addition to applying conventional chemotherapy, the additional administration of an inhibitor of angiogenesis, in particular, an inhibitor of VEGF, such as bevacizumab is beneficial for the treatment of solid tumors, like CRC, BC or GC. Namely, the administration of said inhibitor results in an increase in survival time or survival rate or an increase in favourable clinical outcome. Further, said method allows the identification of subjects with solid tumors, such as CRC where a therapy including the administration of an inhibitor of angiogenesis, in particular, an inhibitor of VEGF, such as bevacizumab, or any one of the angiogenesis inhibitors or VEGF inhibitors identified below, is beneficial for clinical outcome.

Thus, the determination of pretherapeutic serum Ang-2 levels allows prediction of the clinical outcome of CRC, BC or GC patients treated with chemotherapy plus bevacizumab beside the fact that determining the pretherapeutic serum Ang-2 levels allows prediction of the response to bevacizumab containing treatment.

In the context of the present invention, the term "body fluid sample" or "sample of the body fluid" is a biological sample isolated from the subject which can include without being limited thereto, whole blood, serum, plasma, lymphatic fluids, ascetic fluids, interstitial fluids, cerebrospinal fluids, saliva, sputum, sweat, or any other secretion, excretion or other bodily fluids obtained from said individual. Preferably, the body fluid is blood, serum, plasma or urine, in particular, serum or plasma.

A "subject" in the context of the present invention is preferably a mammal. The mammal can be a human, non-human primate, mouse, rat, dog, cat, horse, or cow, but are not limited to these examples. A subject can be male or female. A subject can be one who has been previously diagnosed with or identified as suffering from or having a solid tumor, like CRC, BC or GC and, optionally, but need not have already undergone treatment for said cancer. A subject can also be one who has been diagnosed with or identified as suffering from a solid tumor, such as CRC, BC or GC but who show improvements in the disease as a result of receiving one or more treatments for said cancer. Moreover, a subject may also be one who has not been previously diagnosed or identified as having a solid tumor, such as CRC, BC or GC. For example, a subject can be one who exhibits one or more risk factors for solid tumors, such as CRC, BC or GC or a subject who does not exhibit risk factors for solid tumors, such as colorectal cancer, or a subject who is asymptomatic for solid tumors, such as colorectal cancer. A subject can also be one who is suffering from or at risk of developing solid tumors, such as CRC, BC or GC.

As used herein, the term "solid tumors" refers to cancer types that are derived from epithelial or mesenchymal cells. The most common types of solid tumors are breast cancer, lung cancer, colorectal cancer and prostate cancer. Other solid tumors are gastric cancer, pancreatic cancer, hepatocellula, head and neck cancer, renal cell cancer, cancers of the female reproductive tract like ovarian cancer or endometrial or cervical cancer and germ cell tumors but also skin cancer including basal cell carcinoma, squamous cell carcinoma and malignant melanoma.

The present invention is particularly useful for CRC, BC, GC and skin cancer.

The term "determining" as used herein refers to assessing the presence, absence, quantity, level or amount of either a given substance within a clinical or subject derived sample, including qualitative or quantitative concentration levels of substances or otherwise evaluating the values or categorisation of a subject's clinical parameter.

"Colorectal cancer" or "CRC" according to the present invention refers to cancers that arise in either the colon or the rectum. "Colon cancers" refers to cancers and/or neoplasms that form in a tissue of the colon. Most colon cancers are adenocarcinomas. "Rectal cancer" refers to cancers and/or neoplasms that form in the rectum.

"VEGF inhibitor" as used herein is any substance that decreases signaling by the VEGF-VEGFR pathway. VEGF inhibitors can be, to name just a few examples, small molecules (e.g. tyrosine kinase inhibitors), peptides, polypeptides, proteins, including more specifically antibodies, including anti-VEGF antibodies, anti-VEGFR antibodies, intrabodies, maxibodies, minibodies, diabodies, Fc fusion proteins such as peptibodies, receptibodies, soluble VEGF receptor proteins and fragments, and a variety of others. Many VEGF inhibitors work by binding to VEGF or to a VEGF receptor. Others work more indirectly by binding to factors that bind to VEGF or to a VEGF receptor or to other components of the VEGF signalling pathway. Still other VEGF inhibitors act by altering regulatory posttranslational modifications that modulate VEGF pathway signaling. VEGF inhibitors in accordance with the invention also may act through more indirect mechanisms. Whatever the mechanism involved, as used herein, a VEGF inhibitor decreases the effective activity of the VEGF signaling pathway in a given circumstance over what it would be in the same circumstance in the absence of the inhibitor.

A great many VEGF inhibitors have been described in the literature that may be used in the various embodiments of the present invention. The following are among specific VEGF inhibitors that may be used in the invention in this regard: ABT-869 (Abbott) including formulations for oral administration and closely related VEGF inhibitors; AEE-788 (Novartis) (also called AE-788 and NVP-AEE-788) including formulations for oral administration and closely related VEGF inhibitors; AG-13736 (Pfizer) (also called AG-013736) including formulations for oral administration and closely related VEGF inhibitors; AG-028262 (Pfizer) and closely related VEGGF inhibitors; Angiostatin (EntreMed) (also called CAS Registry Number 86090-08-6, K1-4, and rhuAngiostatin) and closely related inhibitors; Avastin™ (Genentech) (also called bevacizumab, R-435, rhuMAB-VEGF, and CAS Registry Number 216974-75-3) and closely related VEGF inhibitors; AVE-8062 (Ajinomoto Co. and Sanofi-Aventis) (also called AC-7700 and combretastatin A4 analog), and closely related VEGF inhibitors; AZD-2171 (AstraZeneca) and closely related VEGF inhibitors; Nexavar® (Bayer AG and Onyx) (also called CAS Registry Number 284461-73-0, BAY-43-9006, raf kinase inhibitor, sorafenib, sorafenib analogs, and IDDBCP150446) and closely related VEGF inhibitors; BMS-387-032 (Sunesis and Bristol-Myers Squibb) (also called SNS-032 and CAS Registry Number 345627-80-7) and closely related VEGF inhibitors; CEP-7055 (Cephalon and Sanofi-Aventis) (also called CEP-11981 and SSR-106462) and closely related VEGF inhibitors; CHIR258 (Chiron) (also called CAS Registry Number 405169-16-6, GFKI, and GFKI-258) and closely related VEGF inhibitors; CP-547632 (OSI Pharmaceuticals and Pfizer) (also called CAS Registry Number 252003-65-9) and closely related VEGF inhibitors such as, for instance, CP-564959; E-7080 (Eisai Co.) (also called CAS Registry Number 417716-92-8 and ER-203492-00 and closely related VEGF inhibitors; 786034 (GlaxoSmithKline) and closely related VEGF inhibitors; GW-654652 (GlaxoSmithKline) and closely related indazolylpyrimidine Kdr inhibitors; IMC-1C11 (ImClone) (also called DC-101 and c-pIC11) and closely related VEGF inhibitors; KRN-951 (Kirin Brewery Co.) and other closely related quinoline-urea VEGF inhibitors; PKC-412 (Novartis) (also called CAS Registry Number 120685-11-2, benzoylstaurosporine, CGP-41251, midostaurin, and STI-412) and closely related VEGF inhibitors; PTK-787 (Novartis and Schering) (also called CAS Registry Numbers 212141-54-3 and 212142-18-2, PTK/ZK, PTK-787/ZK-222584) and closely related anilinophthalazine derivative VEGF inhibitors; SU11248 (Sugen and Pfizer) (also called SU-11248, SU-011248, SU-11248J, Sutent®, and sunitinib malate) and closely related VEGF inhibitors; SU-5416 (Sugen and Pfizer/Pharmacia) (also called CAS Registry Number 194413-58-6, semaxanib, 204005-46-9) and closely related VEGF inhibitors; SU-6668 (Sugen and Taiho) (also called CAS Registry Number 252916-29-3, SU-006668, and TSU-68) and closely related VEGF inhibitors; VEGF Trap (Regeneron and Sanofi-aventis) (also called AVE-0005 and Systemic VEGF Trap) and closely related VEGF inhibitors; Thalidomide (Celgene) (also called CAS Registry Number 50-35-1, Synovir, Thalidomide Pharmion, and Thalomid) and closely related VEGF inhibitors; XL-647 (Exelixis) (also called EXEL-7647) and closely related VEGF inhibitors; XL-999 (Exelixis) (also called EXEL-0999) and closely related VEGF inhibitors; XL-880 (Exelixis) (also called EXEL-2880) and closely related VEGF inhibitors; ZD-6474

(AstraZeneca) (also called CAS Registry Number 443913-73-3, Zactima, and AZD-6474) and closely related anilino-quinazoline VEGF inhibitors; and ZK-304709 (Schering) (also called CDK inhibitors (indirubin derivatives), ZK-CDK, MTGI, and multi-target tumor growth inhibitor) and other closely related compounds including indirubin derivate VEGF inhibitors. Also among VEGF inhibitors in this regard are: Pazopanib, CDP791, Enzastaurin, BIBF 1120, BAY 573952, BAY 734506, XL 184, IMC-1121B, CEP 701, SU 014813, SU 10944, SU 12662, OSI-930, and BMS 582664, and closely related VEGF inhibitors. In addition to the foregoing inhibitors that act directly on VEGF or VEGFR, the following inhibitors have anti-angiogenic properties and can be used in the invention in much the same way as inhibitors that act directly: ZD-6126 (AstraZeneca and Angiogene) (also called CAS Registry Number 219923-05-4, N-acetyl-colchinol phosphate, ANG-453) and closely related VEGF inhibitors such as other inhibitors in the ANG-400 series; Imatinib (Novartis) (also called CAS Registry Number 152459-95-5 and 220127-57-1, Glivec, Gleevec, STI-571, and CGP-57148) and closely related VEGF inhibitors; RAD-001 (Novartis) (also called CAS Registry Number 159351-69-6, RAD-001, SDZ-RAD, Certican, and everolimus) and closely related VEGF inhibitors; and BMS-354825 (Bristol-Myers Squibb) (also called CAS Registry Number 302962-49-8, Src/Abl kinase inhibitor, and dasatinib) and closely related VEGF inhibitors. Also useful in the invention in this are regard are Volociximab, CCI-779, 17-AAG, DMXAA, CI-1040, and CI-1033.

In a further aspect, the present invention relates to a method for predicting clinical outcome or determining the treatment course in a subject with solid tumors, such as CRC, BC or GC, comprising:
a) determining the amount of Ang-2 in at least one body fluid sample of said subject; and
b) predicting the clinical outcome or determining the treatment course based on the amount of Ang-2 present in said body fluid sample.

The term "subject with colorectal cancer (CRC)" refers to a subject being diagnosed as having CRC. CRC may be diagnosed based on conventional methods for diagnosing CRC as known in the art.

Moreover, the present invention relates to a method for monitoring the progression of solid tumors, such as CRC, BC or GC, in a subject comprising:
a) detecting the level or amount of Ang-2 in a first sample from the subject at a first point in time;
b) determining the level or amount of Ang-2 in a second sample from the subject at a second point in time; and
c) comparing the level or amount of Ang-2 determined in step a) to the level or amount detected in step b) or to a reference value.

In particular, the progression of CRC can be monitored by comparing the level or amount of Ang-2, thus, allowing identification of a transition from e.g. stage III to stage IV of the staging system applied in CRC diagnosis.

Further, the present inventors recognized that the amount of Ang-2 represents a valuable tool, namely, a valuable biomarker for diagnosing or identifying advanced CRC, namely CRC of stage IV as defined in Table 1. Said method comprises the step of
a) determining the level or amount of Ang-2 in a body fluid sample of the subject; and
b) comparing the level or amount determined in step a) to a reference value, wherein an increase in the level or amount relative to the reference value is indicative for advanced CRC.

In a preferred embodiment of the methods according to the present invention, the sample of the subject is a urine, serum, plasma or whole-blood sample, in particular, a serum or plasma sample. In another preferred embodiment, the level or amount of Ang-2 protein is determined in said sample.

A person skilled in the art will appreciate that a number of different methods are useful for determining the level of the relevant proteins of the invention. In one embodiment, protocols for determining the level of protein use agents that bind to Ang-2, like antibodies, antibody fragments, phage display proteins, aptamers, affibodies, chemical lingands, peptides, and combinations thereof.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', F(ab')2, scFv, dsFv, ds-scFv, dimers, minibodies, diabodies, and multimers thereof and bispecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

Antibodies having specificity for Ang-2 may be prepared by conventional methods. A mammal, (e.g. a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

In a preferred embodiment, the antibodies having specificity for Ang-2 do not cross-react with Ang-1.

In one embodiment of the invention, the agents, such as antibodies, antibody fragments, phage display proteins, aptamers, affibodies, chemical ligands or peptides that bind to Ang-2, are labelled with a detectable marker.

The label is preferably capable of producing, either directly or indirectly, a detectable signal. For example, the label may be radio-opaque or a radioisotope, such as $^3H$, $^{14}C$, $^{32}P$, $^{35}S$, $^{123}I$, $^{125}I$ or $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; magnetic or paramagnetic labels, or a metal ion.

In another embodiment, the detectable signal is detectable indirectly. For example, a labelled secondary antibody can be used to detect the protein of interest.

A person skilled in the art will appreciate that a number of other methods are useful to determine the levels of Ang-2 protein in a sample, including immunoassays such as Western blots, ELISA, and immunoprecipitation followed by SDS-PAGE immunocytochemistry. In addition, protein arrays (including microarrays) are useful.

Furthermore, in one embodiment of the invention, additional clinically relevant biomarkers are tested along with Ang-2, such as specific pathogen-associated antigens.

In one embodiment of the invention, Ang-2 protein levels and any additional markers of interest are determined using multiplex technology. This technology has the advantage of quantifying multiple proteins simultaneously in one sample. The advantages of this method include low sample volume, cost effectiveness and high throughput screening. Antibody-based multiplex kits are available from Linco (Millipore Corporation, MA), Bio-Rad Laboratories (Hercules, Calif.), Biosource (Montreal, Canada), and R&D Systems (Minneapolis, Minn.).

The invention also includes the use of kits in predicting a clinical outcome or determining the treatment course in a subject with solid tumors, in particular, with CRC, BC or GC, or for the stratification of a subject with solid tumors, such as CRC, BC or GC, to determine whether said subject is susceptible to the treatment with inhibitors of angiogenesis, in particular, with inhibitors of VEGF, or for monitoring the progression of solid tumors, such as CRC, bC or GC, in a subject, or determining whether a subject has or is at risk of developing advanced stages, like advanced CRC, including a detection agent for Ang-2, typically with instructions for the use thereof. The detection agent may be an antibody, antibody fragment, a phage display protein, an aptamer, affibody, chemical ligand or a peptide. The kit may comprise more than one detection agent. In a further embodiment, the kit includes antibodies directed against Ang-2, optionally with one or more of a medium suitable for formation of an antigen-antibody complex, reagents for detection of the antigen-antibody complexes and instructions for the use thereof. In an additional embodiment, the invention relates to a composition comprising an anti-Ang-2 antibody, optionally provided together in a container.

In a preferred embodiment, the level or amount of angiopoietin-2 is determined by immunological methods, in particular, by ELISA techniques.

That is, in a preferred embodiment, the serum or plasma level of Ang-2 is determined by ELISA.

In the context of the present invention, the term "reference value" refers to an index value, a value derived from one or more CRC risk prediction algorithms or computed indices, a value derived from a subject with the same solid tumor, in particular, with CRC, or a value derived from the subject diagnosed with or identified as suffering from solid tumors, such as CRC. In particular, the reference value is obtained from subjects not afflicted with the same solid tumor, such as CRC and, in addition, the reference value represents a range or index obtained from at least two samples collected from subjects not afflicted with the same solid tumor, such as CRC.

The increase in the level or amount of Ang-2 is for example at least 5%, at least 10%, at least 15%, at least 20%, at least 25% or at least 50% of the reference value or normal control level, preferably, the increase is at least 35%, at least 40% and, most preferably, at least 50%.

When monitoring the progression of a solid tumor, in particular, of CRC, BC or GC, in a subject, the first sample from the subject is preferably obtained prior to being treated for said tumor. Moreover, in another preferred embodiment, the second sample is taken from the subject after being treated for said tumor. Thus, said method allows monitoring the progression of the tumor, such as CRC, BC or GC, in a subject based on detecting the level or amount of Ang-2 e.g. in a body fluid sample, in particular a serum sample.

Moreover, the method according to the present invention allows to determine the success of treating a solid tumor, such as CRC, BC or GC, either by surgery or by applying chemotherapy after surgery or by other post-surgical treatment regimens.

In another preferred embodiment of the present invention, the reference value allowing identification of susceptibility of a subject afflicted with solid tumors, in particular, CRC, BC or GC, to a therapy based on inhibitors of angiogenesis, in particular, an inhibitor of VEGF in combination with a chemotherapy, is below 3.5 ng/ml angiopoietin-2 in a serum sample of said patient. That is, the present inventors recognised that in contrast to the common view, the serum Ang-2 concentrations have an impact on the clinical outcome in patients with solid tumors, such as metastatic CRC, BC, GC, non-small cell lung cancer or renal cell cancer but also skin cancer, like melanoma. In particular, the present inventors recognised the impact of pretherapeutic serum Ang-2 concentrations on the clinical outcome in patients with solid tumors, in particular metastatic solid tumors, such as metastatic CRC under bevacizumab containing therapy. Low serum Ang-2 (serum levels below 3.5 ng/ml angiopoietin-2 in the serum sample) in patients with CRC was associated with significantly increased overall survival (OS) and improved progression free survival (PFS) compared to patients with high pretherapeutic serum Ang-2 (≥3.5 ng/ml in the serum sample). Specifically, the hazard of death was reduced by more than 90% in patients with low serum Ang-2 and the medium PFS was up to three months longer than reported for patients in two pivotal trials combining chemotherapy with bevacizumab. Conversely, for patients with high serum Ang-2 levels, PFS was comparable to the range reported for patients receiving chemotherapy alone. These subjects may be susceptible to a combination treatment of an inhibitor of Ang-2 and an inhibitor of angiogenesis, e.g. an inhibitor of VEGF, such as bevacizumab.

That is, determining the level or amount of Ang-2 in a sample of a body fluid of a subject with solid tumors, such as CRC allows stratification the therapeutic regimen of said subject. Namely, determining the level or amount of Ang-2 in a sample of a subject, like in a sample obtained from the body fluid of said subject allows determining the efficacy of a chemotherapy as such and the type of chemotherapy. Thus, the method according to the present invention allows identifying efficient types of chemotherapy alone in combination with additional therapeutics like inhibitors of angiogenesis and/or inhibitors of Ang-2. In particular, the level of Ang-2 allows to determine whether said subject is susceptible to the treatment with an inhibitor of angiogenesis, in particular, an inhibitor of VEGF. For example, said inhibitor is an inhibitor of VEGF, such as bevacizumab. Determining the level of Ang-2 for example in the serum of said subject, will give the attending physician the possibility to determine and predict the usefulness of therapy based on e.g. bevacizumab or other inhibitors of VEGF but also the specific form of chemotherapy, etc. As demonstrated herein, low serum Ang-2 levels are associated with a better response rate compared to patients with high serum Ang-2 levels. It is noteworthy that the response rate for patients with high serum Ang-2 was similar to the range reported for patients receiving chemotherapy without bevacizumab (Saltz et. al., supra).

In clear contrast to Ang-2, other vascular markers such as tumor MVD (microvessel density) and serum VEGF did not correlate with survival or response in a patient cohort as shown in the examples. Similarly, MVD and VEGF expression levels were not prognostic in CRC patients treated with chemotherapy plus bevacizumab or chemotherapy alone in a large phase III trial (Jubb A. M. et. al., J. Clin. Oncol. 2006, 24:217-27).

Based on the findings described herein, it is concluded that pretherapeutic serum Ang-2 levels—unlike serum VEGF or tumor MVD—predict the clinical outcome of CRC patients treated with chemotherapy, in particular, treatment with chemotherapy plus bevacizumab presumably reflecting tumor stromal-derived Ang-2.

Important clinical implications arise from the findings described herein. Similar to the k-ras mutation status for EGFR antibody therapy in CRC, pretherapeutic serum Ang-2 could be used to predict patients who are likely to benefit from bevacizumab treatment with regard to disease control and survival. In CRC patients undergoing neoadjuvant therapy where quality of remission correlates with higher rates of secondary resection low serum Ang-2 should help to identify treatment responders. Finally, pretherapeutic measurement of serum Ang-2 should be useful to define a cohort of CRC patients that will benefit from concomitant use of novel Ang-2 inhibiting drugs that are currently in clinical development. That is, said cohort of patients with solid tumors having high Ang-2 serum level will benefit from an combination of Ang-2 inhibitor drugs and inhibitors of angiogenesis, such as bevacizumab.

That is, in a preferred embodiment, the method according to the present invention allows the prediction of the efficacy of inhibitors of angiogenesis, in particular, of VEGF as part of a CRC therapy, in particular, the efficacy of administering an antibody or other inhibitor of VEGF, such as bevacizumab.

Moreover, the method according to the present invention allows the determination of the type of chemotherapy beneficial for treating the solid tumors, such as CRC, BC or GC, of a subject.

Thus, it is possible to differentiate individuals suffering from solid cancer, like CRC, BC or GC, into responder and non-responder for receiving anti-VEGF, like bevacizumab, therapy. That is, determining pre-therapeutic Ang-2 level allows to identify patients who are likely to benefit from bevacizumab therapy.

In a further aspect, the present invention relates to the use of a kit in predicting a clinical outcome or determining the treatment course in a subject with solid tumors, such as CRC, or for the stratification of a subject with solid tumors, in particular with CRC, BC or GC, to determine whether said subject is susceptible to the treatment with inhibitors of angiogenesis, in particular with inhibitors of VEGF, or for monitoring the progression of solid tumors, like CRC in a subject, or is at risk for developing advanced CRC, comprising the means for determining the level or amount of angiopoietin-2 protein in a body fluid sample of a subject to be tested and instructions on how to use said test kit following the methods according to the present invention.

In particular, preferred embodiment, said test kit is an ELISA system allowing determination of e.g. Ang-2 in a serum sample obtained from said patient. The skilled person is well aware of suitable ELISA systems allowing detection of angiopoietin-2.

The above disclosure generally describes the present invention. A more complete understanding can be obtained by reference to the following specific examples of certain embodiments of the invention without being limited thereto.

EXAMPLES

Patients, Material, and Methods

Clinical Samples

A total of 90 patients with colorectal adenocarcinoma and 33 healthy volunteers were studied. One cohort of 56 patients had newly diagnosed CRC of various stages (UICC I-IV). After obtaining informed consent, blood serum and tumor tissue was collected at the time of primary resection. A second cohort of 34 patients had primary or relapsed CRC of advanced stage and received a combination treatment of bevacizumab and chemotherapy either in the context of a clinical trial (AIO 0604, n=15) at the Department of Internal Medicine of the University Hospital of Bochum or without participating in a clinical trial (n=19) at an oncology outpatient clinic affiliated with the Comprehensive Cancer Center of the University Hospital of Cologne. From these patients, blood serum was taken before the start of treatment. Demographical, clinical and histopathological baseline parameters were carefully documented. For patients receiving bevacizumab-containing therapy, the clinical response after 2 months of treatment was evaluated according to response evaluation criteria in solid tumors (RECIST). All patients were continuously monitored during the course of treatment and disease progressions and deaths occurring during and after therapy were recorded.

Serum Sample Analysis

Quantikine Immoassays (R&D Systems, USA) were used to measure protein concentrations of Ang-2 and VEGF in blood sera of patients.

Tissue Sample Analysis

Sections of paraffin tissue blocks of CRC specimens were processed for histological analysis as described in Eberhard A et. Al., Cancer Res 60:1388-93, 2000. Tumor blood vessels were stained with the CD34 antibody QBEnd/10 (Novocastra Laboratories, UK) and microvessel density (MVD) was assessed as described previously, Eberhard a et. al., supra.

Immunohistochemistry for Ang-2 was carried out with the following antibodies: MAB 0983 (R&D systems, USA), N18 and F18 (Santa Cruz Biotechnology, USA). To assess non-specific antibody binding, Ang-2 antibodies were blocked by preincubation with recombinant Ang-2 (ratio 1:5, R&D systems, USA) prior to incubation on control sections. A biotinylated secondary antibody, streptavidin peroxidase complex, and diaminobenzidine as a substrate (Zymed, USA) were used to visualize binding of the primary antibody.

For microdissection analysis, cryosections were prepared from adenocarcinoma samples of five patients. Discrete areas of tumor or stromal tissue were microdissected using a laser microbeam (P.A.L.M., Germany). Microdissected tissue areas (each 100 micron in diameter, 30 per slide for stroma and tumor each) were laser-catapulted into a microfuge tube. RNA was extracted using the PicoPure RNA isolation kit (Arcturus, USA) and reverse transcribed using the RevertAid cDNA Synthesis Kit (Fermentas, Lithuania). Real-time-PCR for Ang-2 was carried out using the Light Cycler Fast Start DNA Master Plus Mix (Roche Diagnostics, Switzerland). Results were normalized to a dilution series of prequantified pooled PCR products with the RelQuant Software (Roche Diagnostics, Switzerland). Primer sequences for human and murine specific amplification of Ang-2 and β-actin were as published Thijssen V L, et. al., Exp Cell Res 299:286-93, 2004.

Statistical Analysis

SPSS 17 software (SPSS Inc., USA) was used for data analysis. Overall and progression-free survival was calculated using the Kaplan-Meier method. The log-rank test was used to compare survival times between groups. A Cox regression model was applied to calculate hazard ratios. Parameters others than survivorship were compared using the Mann-Whitney test, the Kruskal-Wallis test and the $\chi 2$ test. All statistical tests were two-sided. Statistical significance was defined as $p<0.05$.

Xenograft Experiments

All animal experiments were performed in accordance with the German animal protection law. The colon carcinoma cell line LS174T was purchased from ATCC (USA) to establish xenografts in nude mice. $5 \times 10^6$ LS174T cells were injected subcutaneously into the flank region of male BALB/cA nude mice (Taconic, Denmark). Animals were sacrificed after tumor size had reached 10 mm in diameter.

For gene expression analysis, tumors were suspended in RNAlater (Qiagen, Germany). RNA was extracted using the NucleoSpin RNA extraction kit (Macherey Nagel, Germany). Reverse transcription and qRT-PCR was performed as described above.

Cell Culture Experiments

The colon carcinoma cell lines LS174T, HT29, DLD-1 and SW948 were cultured in VLE RPMI 1640 (Biochrom, Germany) supplemented with 10% FCS. Human umbilical vein endothelial cells (HUVEC) were purchased from Promocell (Germany) and grown in endothelial cell growth medium (Promocell, Germany). All cell lines were maintained at 37° C. and 5% $CO_2$ except for one experiment involving exposure to controlled hypoxia (1% $O_2$, 5% $CO_2$, balanced $N_2$) for 24 hours.

For Western blot analysis, cytosolic extracts of cultured cells were prepared as described in Kashkar H, et. al., Cell Death Differ 9:750-7, 2002. Equal amounts (100 µg) of protein were separated by SDS-PAGE, transferred to a nitrocellulose membrane (Schleicher & Schuell, Germany), and probed with Ang-2 antibody (F18, Santa Cruz Biotechnology, USA). Primary antibodies were detected using a horseradish peroxidase-conjugated secondary antibody (1:2000; Dako, Germany) and visualized with the ECL-system (Amersham Biosciences, USA). Culture supernatants of CRC cell lines were analysed for Ang-2 protein concentrations using Quantikine Immunoassays (R&D Systems, USA).

Results

Patient Characteristics

Following approval by the Ethics Committees of the Universities of Cologne and Bochum we studied Ang-2 in CRC by enrolling a total of 90 patients with colorectal adenocarcinoma and 33 healthy volunteers. The patient characteristics are summarized in Table 2

TABLE 2

| Patients characteristics | N (%) |
| --- | --- |
| patients | 90 (100.0) |
| sex | |
| male | 54 (60.0) |
| female | 36 (40.0) |
| age | |
| median (years) | 69 |
| range (years) | 45-86 |
| <65 years | 31 (34.4) |
| ≥65 years | 59 (65.6) |
| stage (UICC)[1] | |
| I | 3 (3.3) |
| II | 30 (33.3) |
| III | 15 (16.7) |
| IV | 42 (46.7) |
| systemic therapy | |
| unmonitored[2] | 56 (62.2) |
| monitored[3] | 34 (37.8) |
| 5FU/FO + BV | 1 (1.1) |
| FOLFOX + BV | 4 (4.4) |
| FOLFIRI + BV | 13 (14.3) |
| XELOX + BV | 6 (6.7) |
| XELIRI + BV | 9 (10.9) |
| CAP + BV | 1 (1.1) |
| controls | 33 |

[1] at enrolment
[2] patients with primary CRC who underwent tumor resection and were not monitored for outcome of any further treatment
[3] patients with primary or relapsed CRC who received BV-containing therapy and were monitored for treatment outcome
BV: bevacizumab,
5FU/FO: 5-fluorouracil/folinic acid,
FOLFOX: 5FU/FO/oxaliplatin,
FOLFIRI: 5FU/FO/irinotecan,
XELOX: capecitabine/oxaliplatin,
XELIRI: capecitabine/irinotecan,
CAP: capecitabine Upon enrolment, 34 patients with UICC stage IV were treated with bevacizumab in combination with chemotherapy and monitored for clinical outcome. Seventy-four percent of the patients were treatment-naïve and nine patients had received prior therapy without bevacizumab. Nineteen patients responded to treatment while the rest had stable or progressive disease. The overall progression-free survival (PFS) was 10.6 months. After a median follow-up period of 16.6 months, the median overall survival (OS) had not been reached and 25 of the 34 patients were still alive. No statistically significant differences in survival times and response rates were found between different study sites, gender or age groups.

Ang-2 is Exclusively Expressed in the Tumor Stromal Compartment

Immunohistochemical analysis of Ang-2 with three different commercial Ang-2 antibodies produced ambiguous results concerning the tissue localisation in human CRC Therefore, laser-captured microdissection was used to carefully isolate the tumor and stromal compartments from tissue sections of five CRC patients and examined Ang-2 mRNA expression by qRT-PCR. Ang-2 mRNA expression was clearly detectable in the dissected stromal compartment, but not in the tumor cell compartment. To further verify this, xenografts of CRC in nude mice are generated. In these animals the stromal compartment is of murine origin and the tumor cell compartment is of human origin (LS174T colon carcinoma cells). Using species-specific RT-PCR, Ang-2 mRNA expression was found to be exclusively of stromal (murine) origin.

Figure 1:
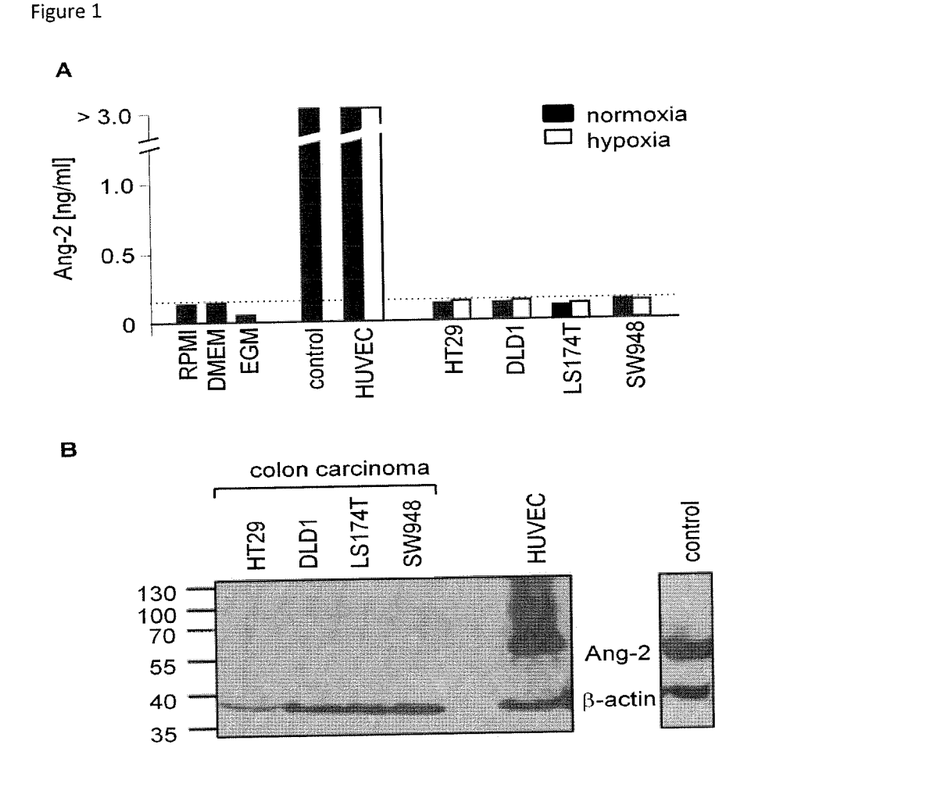
FIG. 1: Expression of Ang-2 in CRC. A: Quantification of Ang-2 protein by ELISA in supernatants of colon carcinoma cell lines, cell culture medium (negative control) and human umbilical vein endothelial cells (HUVEC) and 293FT cells transfected with Ang-2 expression plasmid (positive controls). B: Western blot analysis of cytosolic extracts of colon carcinoma cell lines and HUVEC or 293 FT cells overexpressing Ang-2.

While cultured human umbilical vein endothelial cells (HUVEC) expressed and secreted Ang-2 as detected by Western blot or ELISA, no significant amount of Ang-2 protein was detectable in cytosolic extracts or culture supernatants of various colon carcinoma cell lines (LS174T, HT29, DLD-1, SW948). Following hypoxic cell culture conditions for 24 hours to mimic the microenvironmental conditions within a tumor mass, Ang-2 secretion by colon carcinoma cells was not upregulated (FIG. 1A-B).

Serum Ang-2 Levels are Elevated in Patients with Metastatic Disease

Figure 2:
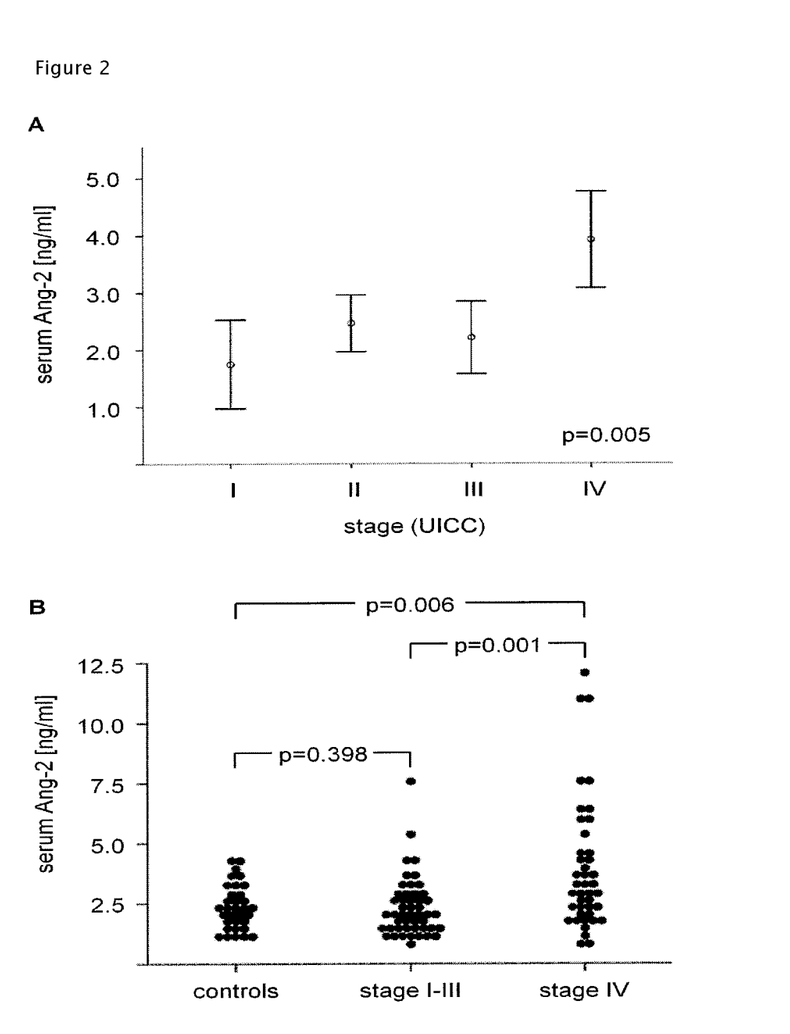
FIG. 2: Serum levels of Ang-2 measured by ELISA in CRC patients. A: Serum Ang-2 according to UICC stages I-IV. B: Serum Ang-2 in healthy controls, non-metastatic (stage I-III) and metastatic disease (stage IV).

Serum levels of Ang-2 in CRC patients increased with advanced tumor stages (p=0.005) (FIG. 2A). Ang-2 concentrations ranged from 0.7 to 12.1 ng/ml (mean: 3.1 ng/ml). The greatest variability was observed in patients with metastatic disease (FIG. 2B). In UICC stage IV patients, serum Ang-2 levels were significantly higher compared to patients with UICC stage I-III or healthy controls (3.9 vs. 2.3 ng/ml, p=0.001, and 3.9 vs. 2.4 ng/ml, p=0.006, respectively). In contrast, serum Ang-2 levels did not differ significantly between UICC stage I-III patients and controls. There was no correlation between serum Ang-2 concentrations, serum levels of VEGF (mean: 3.0 pg/ml) and MVD (mean: 35/HPF).

Low Serum Ang-2 Levels Identify a Patient Population with Better Overall Survival Thirty-four patients of UICC stage IV receiving bevacizumab-containing treatments were dichotomized into subgroups with low (<3.5 pg/ml) or with high (≥3.5 pg/ml) serum Ang-2 concentrations, using the median pretherapeutic serum Ang-2 level as a cut-off value. Similarly, patients were subgrouped into those with low or with high serum VEGF levels (<1.9 pg/ml vs. ≥1.9 pg/ml) and into those with low or with high tumor MVD (<42/HPF vs. ≥42/HPF) using the corresponding median values.

Figure 3:
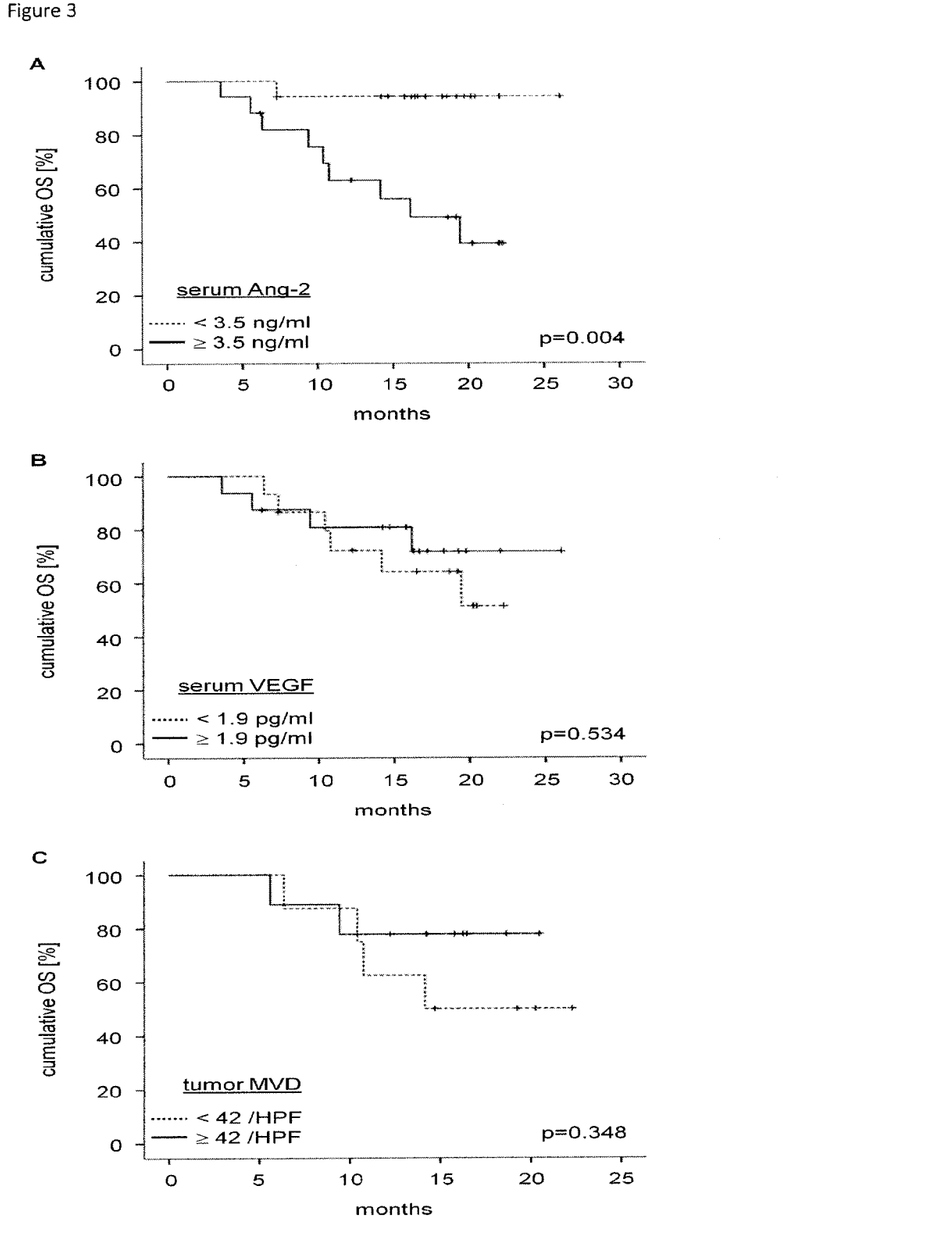
FIG. 3: Overall survival (OS) for CRC patients receiving bevacizumab-containing therapy. A: OS by pretherapeutic serum Ang-2. B: OS by pretherapeutic serum VEGF. C: OS by tumor MVD.

Overall survival was significantly prolonged in patients with low pretherapeutic serum Ang-2 levels (median OS: not reached) compared to the group of patients with high pretherapeutic serum Ang-2 (median OS: 16.2 months, p=0.004). Survival rates at 1.5 years were 94% versus 53% in the low and high serum Ang-2 group, respectively (FIG. 3A). The hazard of death in low Ang-2 patients was decreased by 91% compared to patients with high serum Ang-2 levels (HR 0.09, 95%-CI 1-0.01-0.70, p=0.02). By contrast, there was no significant difference in OS between patients with low and high serum VEGF or tumor MVD (FIG. 3B-C).

Figure 4:
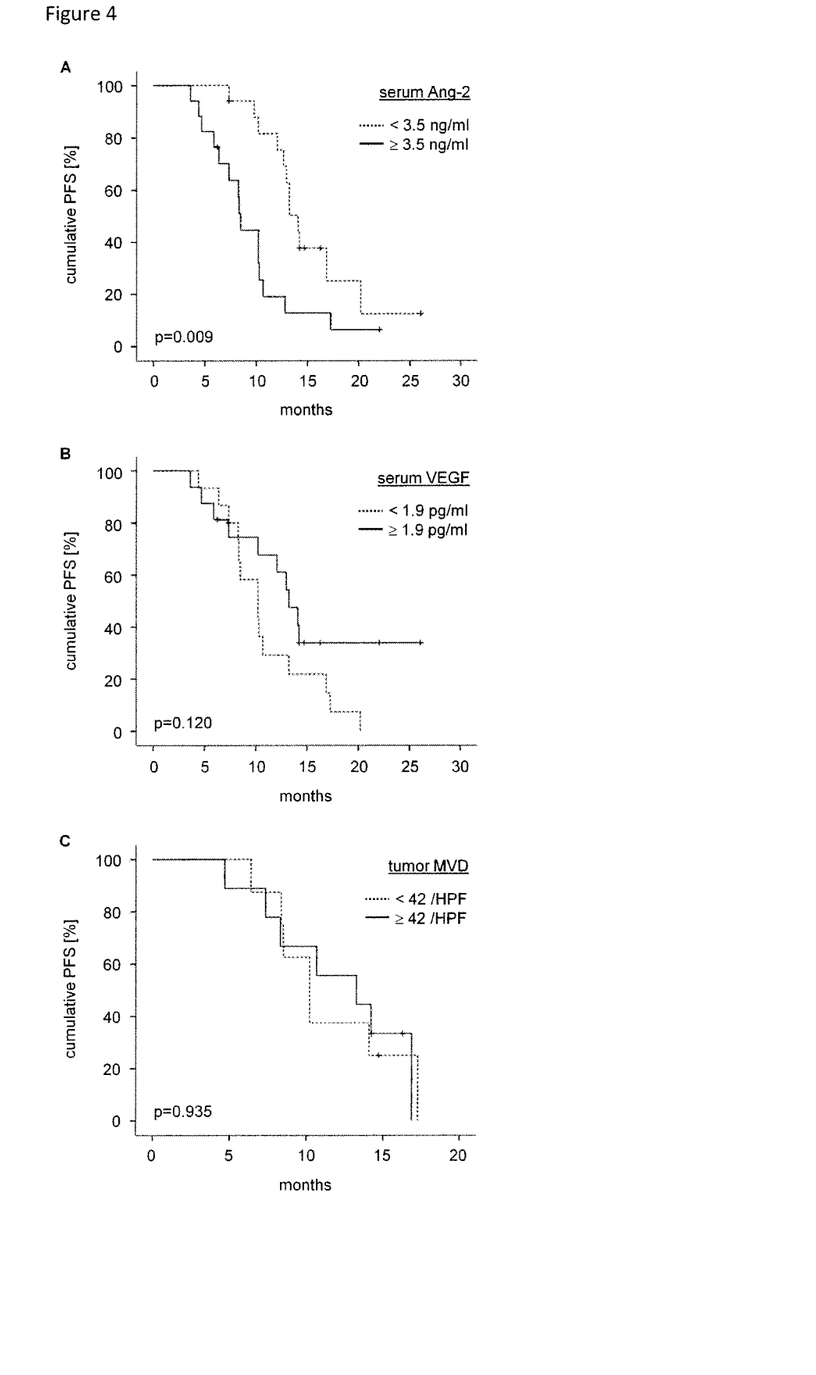
FIG. 4: Progression-free survival (PFS) for CRC patients receiving bevacizumab-containing therapy. A: PFS by pretherapeutic serum Ang-2. B: PFS by pretherapeutic serum VEGF C: PFS by tumor MVD.

Low Serum Ang-2 Levels Identify a Patient Population with Better Progression-Free Survival and Treatment Response Disease control with bevacizumab-containing treatments was better in patients with low pretherapeutic serum Ang-2 levels than in patients with high pretherapeutic serum Ang-2 (median PFS: 12.6 vs. 8.5 months, p=0.009) (FIG. 4A). There was a reduction of 63% in the hazard of progression for patients with low serum Ang-2 compared to those with high serum Ang-2 (HR 0.37, 95%-CI 1-0.17-0.80, p=0.01). Serum VEGF levels prior to therapy did not correlate with PFS (FIG. 4B). Likewise, there was no difference in PFS for patients with low or high tumor MVD (FIG. 4C).

Figure 5:
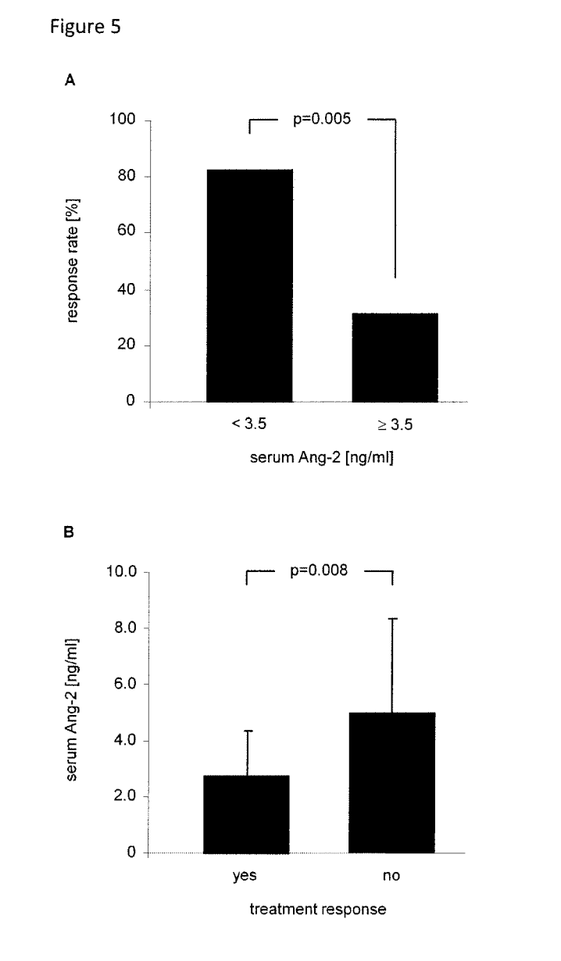
FIG. 5: Treatment response in CRC patients receiving bevacizumab-containing therapy. A: Response rates by pretherapeutic serum Ang-2. B: Pretherapeutic serum Ang-2 in responders and non-responders.

Patients with bevacizumab-containing therapy and low pretherapeutic serum Ang-2 levels had higher response rates than patients with high pretherapeutic serum Ang-2. The response rates in the two groups were 82% and 31% (p=0.005), respectively (FIG. 5A). Mean pretherapeutic serum Ang-2 concentrations were significantly lower in treatment responders compared to non-responders (3.3 ng/ml vs. 5.8 ng/ml, p=0.008) (FIG. 5B). No significant differences were observed in the response rates of patients with low and high serum VEGF or in patients with low and high tumor MVD.

The invention claimed is:

1. A method for treating a solid tumor in a subject with advanced colorectal cancer, comprising
   determining a level of angiopoietin-2 (Ang-2) in a sample of body fluid obtained from said subject with advanced colorectal cancer prior to treatment for the solid tumor; and
   a) if said level of Ang-2 is less than 3.5 ng/ml, then treating said subject by
      administering to said subject chemotherapy that includes an inhibitor of angiogenesis; and
   b) if said level of Ang-2 is equal to or greater than 3.5 ng/ml, then treating said subject by
      administering to said subject chemotherapy that does not include an inhibitor of angiogenesis.

2. The method of claim 1, wherein said inhibitor of angiogenesis is a vascular endothelial growth factor (VEGF) inhibitor.

3. The method of claim 2, wherein said VEGF inhibitor is an antibody.

4. The method of claim 2, wherein said antibody is the VEGF antibody bevacizumab.

5. The method of claim 1, wherein said determining step is performed multiple times.

6. The method of claim 1, wherein said sample of body fluid is a urine or blood sample.

7. The method of claim 1, wherein the level of Ang-2 is determined at the protein level.

8. The method of claim 1, wherein the level or amount of Ang-2 is determined by immunological methods.

9. The method of claim 8, wherein said immunological method is an ELISA.

10. The method of claim 1, further comprising a step of resectioning said solid tumor.

* * * * *